United States Patent
Kaufman

(10) Patent No.: US 8,162,951 B2
(45) Date of Patent: Apr. 24, 2012

(54) FEMORAL TIBIAL SPREADER WITH TENSOR MEASUREMENT

(75) Inventor: David L. Kaufman, Gainesville, FL (US)

(73) Assignee: Innomed, Inc., Savannah, GA (US)

( * ) Notice: Subject to any disclaimer, the term of this patent is extended or adjusted under 35 U.S.C. 154(b) by 1120 days.

(21) Appl. No.: 12/023,205

(22) Filed: Jan. 31, 2008

(65) Prior Publication Data
US 2009/0198240 A1 Aug. 6, 2009

(51) Int. Cl.
| | |
|---|---|
| A61B 17/58 | (2006.01) |
| A61B 17/60 | (2006.01) |
| A61B 17/00 | (2006.01) |
| A61F 2/00 | (2006.01) |
| A61F 4/00 | (2006.01) |
| A61F 5/04 | (2006.01) |
| G01B 5/00 | (2006.01) |
| G01B 3/16 | (2006.01) |

(52) U.S. Cl. .......... 606/102; 606/90; 606/57; 33/797; 33/807

(58) Field of Classification Search .......... 606/57, 606/90, 102; 33/796, 800, 787, 806–808; 7/128; 81/321
See application file for complete search history.

(56) References Cited

U.S. PATENT DOCUMENTS

| | | | |
|---|---|---|---|
| 2,112,873 A * | 4/1938 | Wright | 81/343 |
| 3,916,907 A | 11/1975 | Peterson | |
| 4,066,082 A | 1/1978 | Arcan et al. | |
| 4,127,112 A * | 11/1978 | Sherlock et al. | 600/587 |
| 5,431,653 A | 7/1995 | Calloway | |
| 5,630,820 A | 5/1997 | Todd | |
| 5,997,545 A * | 12/1999 | Doherty et al. | 606/102 |
| 6,648,896 B2 | 11/2003 | Overes et al. | |
| 6,739,068 B1 * | 5/2004 | Rinner | 33/783 |

FOREIGN PATENT DOCUMENTS
WO WO 2007036699 A1 * 4/2007

OTHER PUBLICATIONS

INNOMED, Inc., "Lombardi Knee Spreader", http://www.innomed.net/knee rets.

* cited by examiner

Primary Examiner — Thomas C. Barrett
Assistant Examiner — David Bates
(74) Attorney, Agent, or Firm — Philip H. Burrus, IV

(57) ABSTRACT

A femoral tibial spreader (100) for spreading adjacent bones includes a radial measurement gauge (111) for providing incidia corresponding to an amount of force being applied to the forward ends (105,106) of the femoral tibial spreader (100). The femoral tibial spreader (100) may be used, for example, to separate the femur (301) and tibia (302) during knee surgery. The radial measurement gauge (111) may be used to determine an amount of force being applied to the femur (301) and tibia (302), for example, by the medial and arterial ligaments. Two handle members (104,109) are squeezed together, which causes the forward ends (105,106) to open. A biasing member (110) allows a measurement extension (108) to pivot towards a handle member under tension, thereby providing a measurement of force applied by the ligaments.

20 Claims, 4 Drawing Sheets

FEMORAL TIBIAL SPREADER WITH TENSOR MEASUREMENT

BACKGROUND

1. Technical Field

This invention relates generally to surgical devices for spreading bones, for example to spread the femur and tibia of a leg in knee surgery, and more particularly to a surgical device, capable of one-handed use, for spreading bones while measuring a tension of ligaments about the bones.

2. Background Art

When human joints, such as knees and hips, become aged, diseased, or damaged, modern medical technology permits replacement with artificial joints. Such replacement surgery permits people who would be bound to a wheel chair or bed to walk and enjoy a higher quality of life.

When surgeons perform replacement surgery, as well as when they perform restorative surgery not involving a prosthetic replacement, numerous measurements must be made. By way of example, ligaments hold the human knee together, including the medial and lateral collateral ligaments disposed on either side of the knee. During many surgical and diagnostic operations, a surgeon must separate the femur and tibia of the knee with a spreader. This separation sometimes requires incisions in the ligaments of the knee such that the tension applied by the ligaments is reduced to allow sufficient femoral-tibial separation. It is helpful to know how force the ligaments are exerting prior to making the incisions.

Femoral-tibial spreader devices, such as those manufactured by Innomed, Inc., are available to facilitate femoral-tibial separation. These devices generally have bone-engaging plates that are placed between the tibia condyles and the femur condyles. The plates are then separated, thereby separating the femur from the tibia. A limitation of such devices is that they are not capable of measuring any forces applied by the surrounding ligaments.

Figure 1:
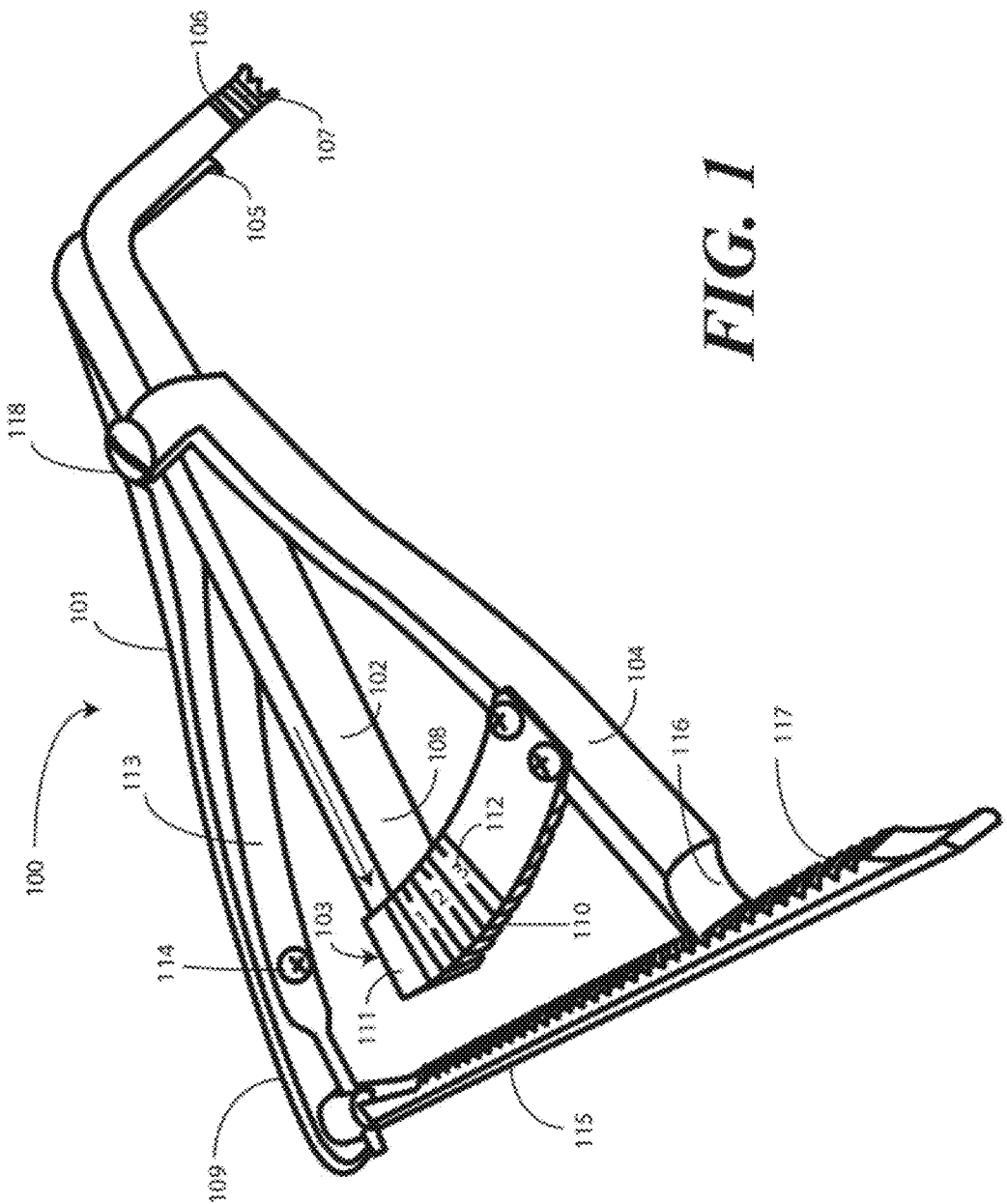
FIG. 1 illustrates a perspective view of one embodiment of a femoral-tibial spreader with a tensor measurement device in accordance with the invention.

Skilled artisans will appreciate that elements in the figures are illustrated for simplicity and clarity and have not necessarily been drawn to scale. For example, the dimensions of some of the elements in the figures may be exaggerated relative to other elements to help to improve understanding of embodiments of the present invention.

DETAILED DESCRIPTION OF THE INVENTION

Embodiments of the invention are now described in detail. Referring to the drawings, like numbers indicate like parts throughout the views. As used in the description herein and throughout the claims, the following terms take the meanings explicitly associated herein, unless the context clearly dictates otherwise: the meaning of "a," "an," and "the" includes plural reference, the meaning of "in" includes "in" and "on." Relational terms such as first and second, top and bottom, and the like may be used solely to distinguish one entity or action from another entity or action without necessarily requiring or implying any actual such relationship or order between such entities or actions. Also, reference designators shown herein in parenthesis indicate components shown in a figure other than the one in discussion. For example, talking about a device (10) while discussing figure A would refer to an element, 10, shown in figure other than figure A.

Figure 2:
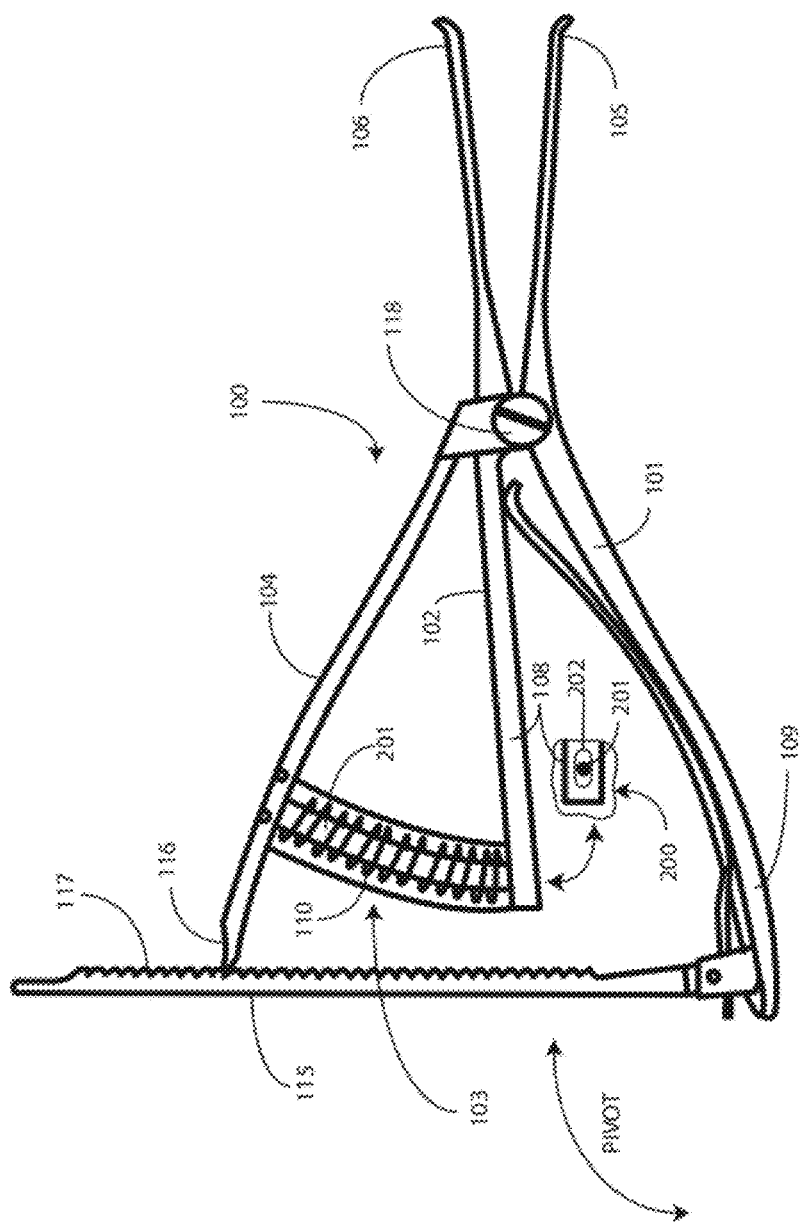
FIG. 2 illustrates a bottom plan view of one embodiment of a femoral-tibial spreader with a tensor measurement device in accordance with the invention.

Turning now to FIGS. 1 and 2, illustrated therein is a perspective view of a femoral-tibial spreader 100, and a bottom plan view of a femoral-tibial spreader 100, respectively, for separating femoral and tibial components of the knee in accordance with embodiments of the invention. The femoral-tibial spreader 100 includes a tension measurement device 103 that can be used to measure, for example, the amount of force being applied by medial and lateral collateral ligaments in a knee joint. The femoral-tibial spreader 100, in one embodiment, is configured for one-handed operation, thereby allowing a doctor to use the other hand for other purposes.

The femoral-tibial spreader 100 includes a first lever 101 and a second lever 102 that are pivotably coupled together at a connection point 118. In one embodiment, the connection point 118 comprises a screw and boss, although other connection devices, including rivets and the like, may also be used.

Each of the first lever 101 and the second lever 102 has a forward end 105,106 for engaging human bone. In the illustrative embodiment of FIGS. 1 and 2, the first lever 101 terminates in the first forward end 105, while the second lever 102 terminates in the second forward end 106. As the forward ends 105, 106 are configured to engage bones, each forward end 105,106 may include surface details suited for that purpose. For instance, serrations or other textured patterns may be applied to the forward ends 105,106 to facilitate better gripping characteristics.

By way of example, in one embodiment, the femoral-tibial spreader 100 of the present invention is used in knee surgery for separating a femur and tibia. As such, the forward ends 105,106 are configured to engage an end of a femur and an end of a tibia of a flexed knee. To accommodate this engagement, in the illustrative embodiment of FIGS. 1 and 2, each forward end 105,106 included an outwardly curved, serrated surface, e.g. surface 107. The outward curves are well suited for engaging rounded femur condyles and tibia condyles, while the serrations ensure that the grip between these condyles is retained.

Opposite the first forward end 105, the first lever 101 terminates in a first handle member 109. The second lever 102 terminates in a measurement extension 108 opposite the second forward end 106. A second handle member 104 is coupled with the first lever 101 and the second lever 102 at the connection point 118. A spring 110 biases the measurement extension 108 radially away from the second handle member 104. When the first handle member 109 and second handle member 104 are squeezed together, the spring 110 applies additional force to the measurement extension 108.

When the forward ends 105,106 are engaging bone members, squeezing the first handle member 109 and the second handle member 104 together tends to make the first forward end 105 and the second forward end 106 separate, as the spring 110 works to push the measurement extension 108 towards the first handle member 109. However, this separation may be offset by forces being applied to the forward ends 105,106 such that the forces are working to move the first forward end 105 towards the second forward end 106. Such a force will cause the spring 110 to compress, meaning that the second handle member 104 will begin to move towards the measurement extension 108. Embodiments of the invention employ this spring compression to provide indicia of an amount of compression of the spring 110.

A radial measurement gauge 111 is coupled to the second handle member 104 in the exemplary embodiment of FIGS. 1 and 2. The radial measurement gauge 111 includes select demarcations 112 that provide the indicia of spring compression. Through calibration in the factory, the demarcations 112 may be set to Newtons, pounds, or other force measurements. As some physicians prefer a simpler scale, in one embodiment the demarcations may be simply designated in grades, for example grade 1, grade 2, grade 3, and so forth. These radial demarcations 112 provide a plurality of measurement indicia, each being indicative of an amount of force being applied to the forward end 105 of the first lever 101 and the forward end 106 of the second lever 102. Such force may be applied, for instance, by a medial or arterial ligaments, or combinations thereof, in a flexed knee between the end of the femur and the end of the tibia.

While the radial measurement gauge 111 may be coupled to either the first handle member 109, the measurement extension 108, or the second handle member 104, in the illustrative embodiment of FIGS. 1 and 2, the radial measurement gauge 111 is rigidly coupled to the second handle member 104. Further, the radial measurement gauge 111 is coupled to the second handle member 104 atop the spring 110. Such placement hides the spring 110 from view when the femoral-tibial spreader 100 is viewed from the top, and can make visibility of the radial measurement gauge 111 better.

A radial compression guide 201 aligns the second handle member 104 with the measurement extension 108. In one embodiment, the radial compression guide 201 comprises a semi-circular piece of metal about which the measurement extension 108 is able to pass. Looking at sectional view 200, the measurement extension 108 includes an aperture 202 through which the radial compression guide 201 passes. This aperture 202 to radial compression guide 201 engagement maintains axial alignment as the first handle member 109 and second handle member 104 are moved together.

The spring 110, in one embodiment, is a coiled spring disposed about the radial compression guide 201. As pressure is placed on the first forward end 105 and the second forward end 106 when the first handle member 109 and second handle member 104 are moved together, this force causes the spring 110 to compress. The spring 110 is held in alignment with the measurement extension 108, and the second handle member 104 by the radial compression guide 201. While the radial compression guide 201 may be coupled to either the first handle member 109 or the second handle member 104, in one embodiment it is rigidly coupled to the second handle member 104. In this configuration, the spring 110 compresses when force is applied to the forward ends 105,106. Thus, the radial compression guide 201 is all that is needed to retain the spring 110 to the femoral tibial spreader 100.

The femoral tibial spreader 100 includes several features that facilitate one-handed operation. One such feature is a leaf spring 113 that is configured, in conjunction with the spring 110, to bias the first handle member 109 and the second handle member 104 apart in a rest state.

In one embodiment, the leaf spring 113 is configured to accomplish this by biasing the measurement extension 108 radially away from the first handle member 109. The leaf spring 113 is fixedly coupled to the first handle member 109 in such a configuration. In the exemplary embodiment of FIGS. 1 and 2, the leaf spring 113 is coupled to the first handle member 109 by a screw, although rivets, spot welds, or other fastening means may also be used.

A second feature that facilitates one-handed operation is the inclusion of a retainer 115. The retainer 115 spans between the first handle member 109 and the second handle member 104 and is configured to retain the first handle member 109 in a fixed radial or axial alignment relative to the second handle member. In the illustrative embodiment of FIGS. 1 and 2, the retainer 115 is pivotally coupled to the first handle member 109. (Note that the retainer 115 could have equally been pivotally coupled to the second handle member 104 as well.) To provide a semi-locking mechanism for the retainer 115, so as to keep it from flopping about willy-nilly, in one embodiment the retainer 115 is spring-loaded. In the illustrative embodiment of FIGS. 1 and 2, the retainer 115 is spring loaded by the leaf spring 113.

The second handle member 104 terminates in an engaging member 116. The engaging member 116 is configured to engage the retainer 115 so as to retain the first handle member 109 and the second handle member 104 in s fixed radial alignment. In one embodiment, the retainer 115 includes a serrated surface 117. The serrated surface 117 includes a plurality of ramps over which the engaging member 116 passes as the first handle member 109 and the second handle member 104 are squeezed together. The engaging member 116 engages the serrated surface 117 so as to keep the first handle member 109 and second handle member 104 from re-opening. To re-open the device, one simply pivots the retainer 115 down and away from the measurement extension 108.

Figure 3:
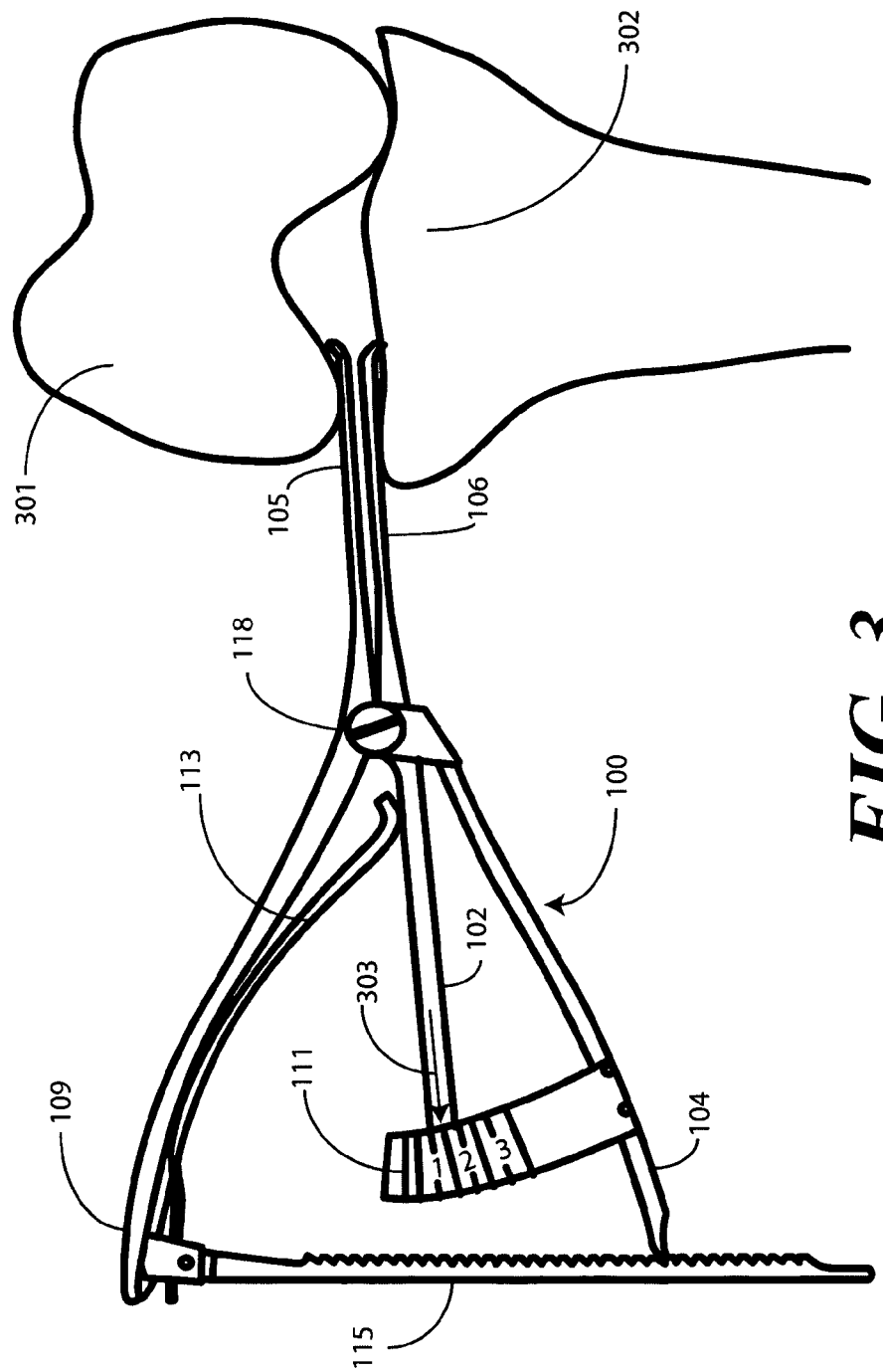
FIG. 3 illustrates one embodiment of a femoral-tibial spreader in accordance with the invention engaging a tibia condyles and the femur condyles in accordance with the invention.

Turning now to FIG. 3, illustrated therein is the femoral tibial spreader 100 in action. In FIG. 3, the femoral tibial spreader 100 is operating as a spreader for separating adjacent bones 301,302. The first handle member 109 and second handle member 104 serve as pivotably coupled handles moving about the pivot point 118. One of the pivotably coupled handles, specifically the first handle member 109 in the illustrative embodiment of FIG. 3, terminates in a forward end 105 that operates as a bone engagement member.

The second lever 102 functions as a measurement arm, and is pivotally coupled with the handle members 109,104 at the pivot point 118. The second lever 102 terminates at the second forward end 106, which works as a second bone engagement member. The second lever 102 is biased pivotally away from the second handle member 104 by a spring (110), which functions as a biasing device.

The radial measurement gauge 111 is fixedly coupled to the second handle member 104 and is configured to provide indicia of a radial displacement between the second lever 102 and the second handle member 104. The leaf spring 113 operates as a second biasing device and is coupled to the first handle member 109. The leaf spring 113 is configured to bias the second lever 102 pivotably away from the first handle member 109. The retainer 115 is coupled to the first handle member 109 and is configured to retain the first handle member 109 and the second handle member 104 in a fixed orientation when squeezed together.

The forward ends 105,106 of the femoral tibial spreader 100 are configured to engage ends of the first and second bones 301,302. When the first handle member 109 and second handle member 104 are squeezed together, the first bone 301 and second bone 302 begin to separate. This separation continues until external pressure, perhaps from ligaments holding the first bone 301 and second bone 302 together, equals that of the spring (110). When this occurs, the spring (110) starts to compress, thereby causing the second lever 102 to pivot towards the second handle member 104. An arrow 303 on the second lever 102, operating in concert with the radial measurement gauge 111, then provides indicia as to how much pressure is being exerted on the two bones 301,302. A user knows this because there is a point at which further squeezing of the first handle member 109 and second handle member 104 begins to cause the first bone 301 and second bone 302 so continue to separate. It is at this balance point that the pressure exerted by ligaments may be measured.

Figure 4:
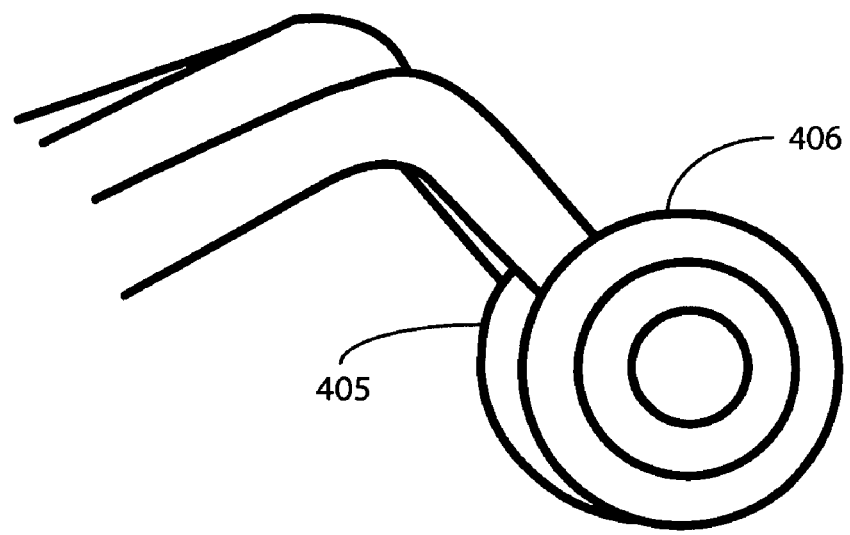
FIGS. 4-5 illustrate various forward ends for use with a femoral-tibial spreader in accordance with embodiments of the invention.
Figure 5:
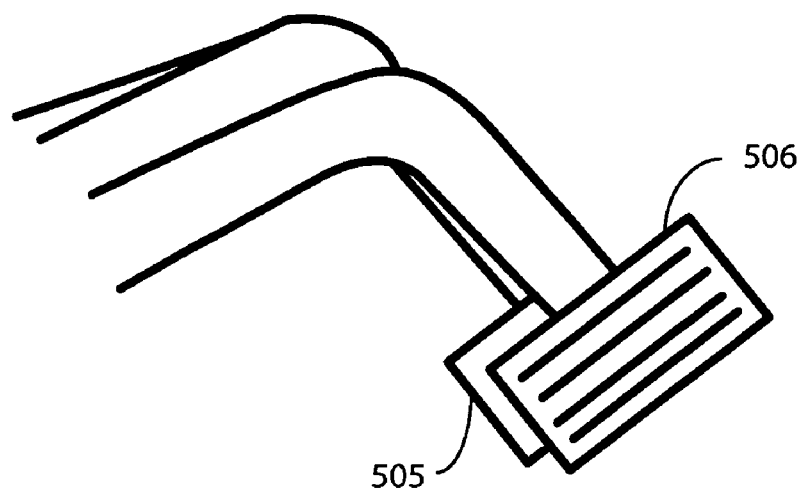

Turning now to FIGS. 4 and 5, illustrated therein are alternate forward ends for use with a femoral-tibial spreader in accordance with embodiments of the invention. Just as no two people are exactly alike, no two knee surgeries are exactly alike. While the outwardly curved, serrated forward ends of FIGS. 1-3 work well in many applications, some bone types will require alternate forward ends. In FIG. 4, the forward ends 405,406 comprise textured discs. In FIG. 5, the forward ends 505,506 comprise textured, rectangular plates. Either of these forward end configurations may be manufactured from metal, plastic, or encapsulated metal, such as stainless steel coated in rubber or plastic.

In the foregoing specification, specific embodiments of the present invention have been described. However, one of ordinary skill in the art appreciates that various modifications and changes can be made without departing from the scope of the present invention as set forth in the claims below. Thus, while preferred embodiments of the invention have been illustrated and described, it is clear that the invention is not so limited. Numerous modifications, changes, variations, substitutions, and equivalents will occur to those skilled in the art without departing from the spirit and scope of the present invention as defined by the following claims. Accordingly, the specification and figures are to be regarded in an illustrative rather than a restrictive sense, and all such modifications are intended to be included within the scope of present invention.

What is claimed is:

1. A spreader for separating adjacent bones, the spreader comprising:
    pivotably coupled handles coupled at a pivot point, one of the pivotably coupled handles terminating in a first bone engagement member;
    a measurement arm, directly and pivotably coupled with the pivotably coupled handles at the pivot point, the measurement arm terminating in a second bone engagement member;
    a biasing device biased against one of the handles and the measurement arm, and configured to bias the measurement arm pivotably away from one of the pivotably coupled handles; and
    a measurement gauge fixedly coupled to one of the pivotably coupled handles or the measurement arm, the measurement gauge being configured to provide indicia of radial displacement between the measurement arm and one of the pivotably coupled handles.

2. The spreader of claim 1, further comprising a second biasing device coupled to one of the pivotably coupled handles or the measurement arm, the second biasing device being configured to bias the measurement arm pivotably away from one of the pivotably coupled handles.

3. The spreader of claim 1, further comprising a retainer coupled to one of the pivotably coupled handles and configured to retain at least the pivotably coupled handles in a fixed orientation.

4. A femoral tibial spreader for separating femoral and tibial components of a knee, comprising:
    a first lever and a second lever, pivotably coupled together at a connection point and disposed on a first side of the connection point, the first lever and the second lever each comprising a forward end for engaging human bone extending from the first and second levers and disposed on a second side of the connection point opposite the first side, the first lever comprising a first handle member disposed opposite the forward end of the first lever on the first side of the connection point, the second lever comprising a measurement extension disposed opposite the forward end of the second lever on the first side of the connection point;
    a second handle member pivotably coupled with the first lever and the second lever at the connection point and disposed on the first side of the connection point;
    a first spring biasing the measurement extension radially away from the second handle member;
    a second spring configured to bias the measurement extension radially away from the first handle member; and
    a radial measurement gauge configured to provide indicia of an amount of compression of the first spring.

5. The femoral tibial spreader of claim 1, further comprising a radial compression guide aligning the second handle member and the measurement extension, the measurement extension being able to pass along the radial compression guide.

6. The femoral tibial spreader of claim 5, wherein the spring comprises a coiled spring disposed about the radial compression guide.

7. The femoral tibial spreader of claim 5, wherein the radial measurement gauge is rigidly coupled to one of the first handle member or the second handle member.

8. The femoral tibial spreader of claim 7, wherein the radial measurement gauge is coupled to the second handle member and is proximately located with the radial compression guide.

9. The femoral tibial spreader of claim 1, wherein the radial measurement gauge comprises radial demarcations providing a plurality of measurement indicia, each measurement indicia being indicative of an amount of force being applied to the forward end of the first lever and the forward end of the second lever.

10. The femoral tibial spreader of claim 1, wherein the second spring comprises a leaf spring.

11. The femoral tibial spreader of claim 10, wherein the leaf spring is fixedly coupled to the first handle member.

12. The femoral tibial spreader of claim 1, further comprising a retainer having a serrated surface configured to retain the first handle member and the second handle member in a retained radial alignment.

13. The femoral tibial spreader of claim 12, wherein the retainer is pivotably coupled to one of the first handle member or the second handle member.

14. The femoral tibial spreader of claim 13, wherein the retainer is pivotably coupled to the first handle member, wherein the second handle member terminates in an engaging member configured to engage the serrated surface.

15. The femoral tibial spreader of claim 12, further comprising a leaf spring coupled to the first handle member so as to bias the measurement extension radially away from the first handle member, wherein the retainer is spring-loaded by the leaf spring.

16. The femoral tibial spreader of claim 1, wherein the forward end of the first lever and the forward end of the second lever are configured to engage an end of a femur and an end of a tibia of a flexed knee, such that when the first handle member and the second handle member are radially moved together, the end of the femur and the end of the tibia separate.

17. The femoral tibial spreader of claim 16, wherein the radial measurement gauge comprises a plurality of demarcations indicative of an amount of pressure being applied by a medial and arterial ligament of the flexed knee to the end of the femur and the end of the tibia.

18. The femoral tibial spreader of claim 1, wherein the forward end of the first lever and the forward end of the second lever each comprise an outwardly curved, serrated surface.

19. The femoral tibial spreader of claim 1, wherein the forward end of the first lever and the forward end of the second lever each comprise a textured, rectangular plate.

20. The femoral tibial spreader of claim 1, wherein the forward end of the first lever and the forward end of the second lever each comprise a textured disc.

* * * * *